United States Patent [19]

Römhild et al.

[11] Patent Number: 4,820,154

[45] Date of Patent: Apr. 11, 1989

[54] DENTAL INSTRUMENT WITH A TOOL FOR TREATING THE TEETH

[75] Inventors: Ludwig Römhild, Am Kugelfeld 3, Berchtesgaden, Fed. Rep. of Germany; Erwin Hartmann, Möriken; Peter Reinhard, Weingartenstrasse 8, Spreitenbach, both of Switzerland

[73] Assignees: Ludwig Römhild, Berchtesgaden, Fed. Rep. of Germany; Peter Reinhard, Spreitenbach, Switzerland

[21] Appl. No.: 33,522

[22] Filed: Apr. 1, 1987

[30] Foreign Application Priority Data

Apr. 2, 1986 [CH] Switzerland .................. 1290/86

[51] Int. Cl.⁴ .................................................. A61C 1/14
[52] U.S. Cl. .................................... 433/128; 433/119; 433/143; 279/80; 279/97
[58] Field of Search ............... 433/118, 119, 143, 126, 433/127, 128; 279/113, 74, 82, 80, 97

[56] References Cited

U.S. PATENT DOCUMENTS

| | | | |
|---|---|---|---|
| 2,751,229 | 6/1956 | Schultz | 279/82 |
| 2,807,473 | 9/1957 | Kiehne | 279/82 |
| 4,502,824 | 3/1985 | Dohse et al. | 279/1 B |
| 4,634,376 | 1/1987 | Mossle et al. | 433/118 |

Primary Examiner—Carroll B. Dority, Jr.
Attorney, Agent, or Firm—Helfgott & Karas

[57] ABSTRACT

A dental instrument employs a tool having an upper portion for use in contacting teeth and a lower portion defining a shank with a lower end, a hollow elongated gripping holder having an opening at one end, a device in the holder communicating with the opening in the holder to removably receive said part of the shank, including the lower end; and a manually operated coupling mechanism having a first section connected to the holder and a second section on the shaft, the mechanism having a lock position at which the first section engages the second section in such a manner that the tool is locked in the holder in position for use, and having a release position at which the first and second sections are disengaging and the tool can be removed from the holder.

17 Claims, 2 Drawing Sheets

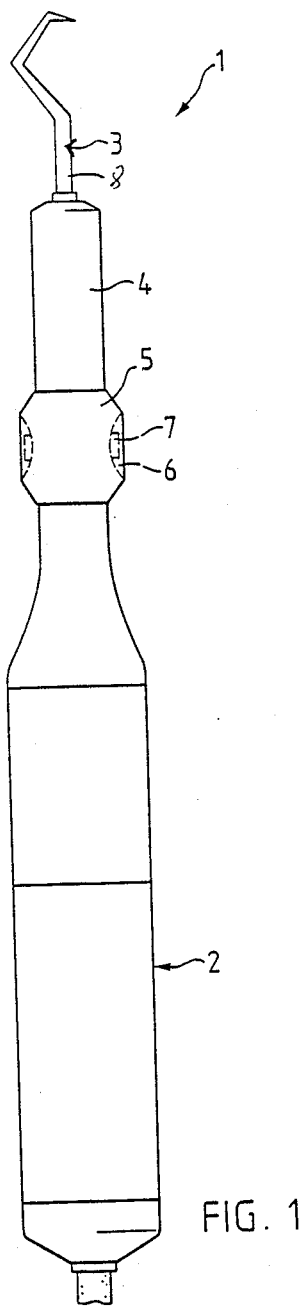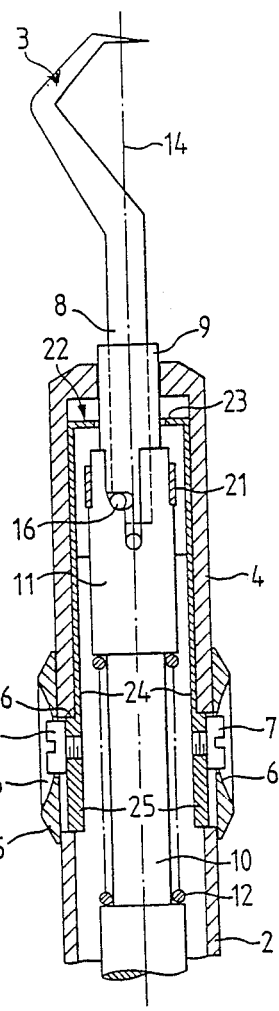
FIG. 1
FIG. 2

DENTAL INSTRUMENT WITH A TOOL FOR TREATING THE TEETH

BACKGROUND OF THE INVENTION

The invention relates to a dental instrument with a tool for treating teeth, the tool being fixed in a gripping shaft and is also removable therefrom.

Dental instruments for manually working on teeth are known in numerous different forms. In the simplest constructional embodiment the dental instrument is constituted by a single piece formed by a gripping shaft and a tool. As it is necessary to use tools of different shapes and sizes when treating teeth, it is necessary to have a correspondingly large number of instruments. These instruments also include those in which although the gripping shaft and tool are constituted by two parts, said parts are not detachably joined together.

In addition, two-part dental instruments are known, in which the gripping shaft and tool are interconnected in a detachable manner, either manually or by using a wrench. In the first embodiment the connection is brought about by a collet, which requires additional securing against the tool twisting. By turning a sleeve it is possible to fix or release the tool with respect to the gripping shaft. Thus, the tool can be replaced without difficulty if breakage occurs of it becomes worn.

This also applies with respect to the second embodiment, in which onto the base part of the tool are shaped a taper sleeve and to the latter a threaded bolt. The taper sleeve and threaded bolt can be screwed into a tapped hole provided in the gripping shaft with a taper shaped onto the mouth of the hole and can be fixed with a wrench. This solution also makes it possible to replace the tool without difficulty.

As it is an unavoidable requirement of dental instruments of the aforementioned type that the gripping shaft and the tool are reliably interconnected, so that in part very considerable force exerted when treating the teeth, particularly in the direction of the shaft axis and in the circumferential direction, can be applied without any relative movement between the gripping shaft and the tool. Thus, the instrument with the collet requires an additional securing means to prevent twisting and the other instrument requires a securing cone or tape.

SUMMARY OF THE INVENTION

The problem of the present invention is to so construct a dental instrument of the aforementioned type, that it is possible to extremely rapidly replace the tool and it is possible to reliably ensure a firm immovable connection between gripping shaft and tool under all stressing conditions. A dental instrument in accordance with the principles of this invention employs a tool having an upper portion for use in contacting teeth and a lower portion defining a shank with a lower shaft and a lower end. The instrument also employs a hollow elongated gripping holder having an opening at on end. First means in the holder communicates with the opening in the holder to removably receive said shank.

A manually operated coupling mechanism includes a first section connected to the holder and a second section on the shank. The mechanism has a lock position at which the first section engages the second section in such a manner that the tool is locked immovably in position for use. The mechanism has a release position at which the first and second sectins are disengaged and the tool can be removed from the holder.

The aforementioned objects and advantages of the invention as well as other objects and advantages thereof will either be explained or will become apparent to those skilled in the art when this specification is read in conjunction with the accompanying drawing and specific description of preferred embodiments which follows.

BRIEF DESCRIPTION OF THE DRAWINGS

FIG. 1 is a diagrammatically represented view of a dental instrument in accordance with one embodiment of the invention;

FIG. 2 is a diagrammatically represented partial longitudinal section of the structure shown in FIG. 1;

DETAILED DESCRIPTION OF THE PREFERRED EMBODIMENT

Figure 4:
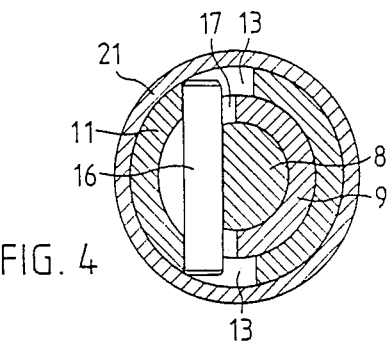
FIG. 4 is a cross-section taken along line IV—IV in FIG. 3.

A dental instrument known as a scaler 1 shown in FIG. 1 has a cylindrical gripping shaft or holder 2 and a tool generally indicated at 3. An actuating ring 5 is displaceably guided on the tool-side end 4 of gripping shaft 2. The displacement of actuating ring 5 and therefore the release and replacement of tool 3 can only take place if inward depression occurs of two pushbuttons 7 provided in depression 6 on the actuating ring 5. Even if only a single pushbutton 7 is depressed, as can unintentionally take place during the treatment of teeth, this does not lead to the separation of tool 3 from gripping shaft 2. The connection between gripping shaft 2 and tool 3 can only be broken on depressing both pushbuttons 7.

The longitudinal section represented in FIG. 2 shows the tool side end 4 of gripping shaft 2 and tool 3. The tool has an upper portion which used in contacting teeth for dental treatment and a lower portion which is a shank or base 8 having a lower end. The shank is inserted in a chuck 9. This chuck is the upper portion or hollow cylinder or rod 10 housed in gripping shaft or holder 2 and on which is displaceably guided a control sleeve 11 counter to the tension of a compression spring 12.

Figure 3:
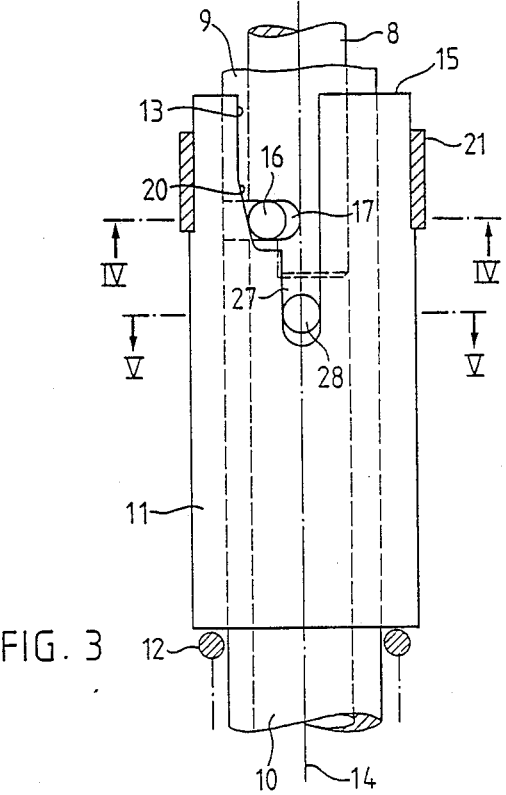
FIG. 3 is a detail view in cross-section of a portion of the structure shown in FIG. 1.

As shown in FIG. 3, two longitudinal slots 13 with different widths face one another in control sleeve 11, extend in the direction of axis 14 of gripping shaft 2 and are open toward the tool-side front face 15.

Figure 6:
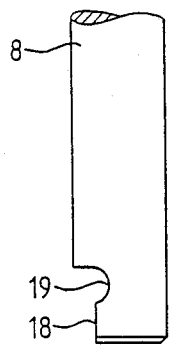
FIG. 6 is a detail view of a portion of the tool used in the instrument of FIG. 1.

As can be gathered from FIG. 4, the ends of a coupling pin 16 project into the two longitudinal slots 13. Coupling pin 16 is located in a groove 17 of chuck 9 which is at right angles to instrument axis 14. According to FIG. 6, at the end of the base part 8 of tool 3 is provided a surface 18, at whose transition to the full base part cross-section there is a groove-like depression 19.

The contour of longitudinal slots 13 has a portion 20 sloping towards the instrument axis 14. If the control sleeve 11 is moved by the tension of compression spring 12 against the tool-side end 4 of griping shaft 2, through the inclined portion 20 of the two longitudinal slots 13 coupling pin 16 is moved into the groove-like depression 19 of base part 8, which corresponds to FIG. 3 and 6. The inclination of sloping portion 20 is such that self-locking occurs between coupling pin 16 and portion 20. As a result of this arrangement of coupling pin 16, there is not only a clearance-free connection between tool 3 and gripping shaft 2, but there can be no detachment of this connection through the forces occurring when treating the teeth. Through the use of coupling pin 16, there is no possibility of tool 3 turning, even if very high circumferential forces occur thereon. A securing or retaining ring 21 on control sleeve 11 prevents the coupling pin 16 from falling out.

As the control sleeve 11 is located in the interior of gripping shaft 2, an acutating sleeve 22 is provided for the actuation thereof and said sleeve has on the tool side an inner flange 23 which, for the displacement of control sleeve 11, acts on the front face 15 thereof. At the end of actuating sleeve 22 remote from inner flange 23 are shaped two elastically deformable arms 24, which are provided at their ends with a reinforced portion 25, with the aid of which arms are supported on the inner rim of openings 26, which are located below the top of the depressions 6 of actuating ring 5. On pressing down the two pushbuttons 7, arms 24 are elastically bent inwards, so that they move away from the inner rim of openings 26 and can therefore be displaced by actuating ring 5. The openings 26 provide clearance for the ring 5 to be slid along the holder away from the tool receiving end to release the shank. The ring can be slid back whereby reinforced portions 25 again snap into openings 26. In the reinforced portions 25 of arms 24 is fixed the pushbutton 7, e.g. in the form of a cheese-head screw, which projects into depression 6 of actuating ring 5.

To prevent rotation of control sleeve 11, a radially directed slot portion 27 is provided in each of the longitudinal slots 13.

Figure 5:
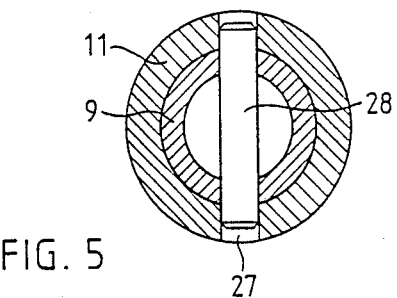
FIG. 5 is a cross-section taken along line V—V in FIG. 3.

The end of a stop pin 28 project into the two slotted portions 27, said pin being fixed in chuck 98, cf. FIG. 5.

The above described connection between the gripping shaft and the tool located in the former has proved to be very reliable and can be used in all manual dental instruments 1. Due to the extremely rapid tool change possibility, this connection can be used in a particularly advantageous manner in mechanical, i.e. power-driven scalers.

While the fundamental novel features of the invention have been shown and described and pointed out, it will be understood that various substitutions and changes in the form of the details of the embodiments shown may be made by those skilled in the art without departing from the concepts of the invention as limited only by the scope of the claims which follows.

We claim:

1. A dental instrument comprising:
   a tool having an upper portion for treating teeth and a lower portion defining a shank;
   a hollow elongated gripping shaft;
   an elongated rod positioned in said shaft and having at an upper end thereof a chuck portion removably receiving said shank;
   a control sleeve displaceably mounted on said rod, said control sleeve having two longitudinal slots, said chuck portion having a groove;
   a coupling pin situated in said groove and extending into said slots to be moved in said slots in a direction normal to an axis of elongation of said shaft for coupling said chuck portion with and releasing said chuck portion from said control sleeve;
   an actuating sleeve positioned in said shaft and having a flange cooperating with said control sleeve and two arms; and
   an actuating ring disposed on said shaft and having two externally actuated push-buttons cooperating with said arms and operated to release said arms to displace said control sleeve from a coupled position with said chuck portion to a release position from said chuck portion, said shank having a groove-like depression engaging said coupling pin when said chuck portion and said control sleeve are in the coupled position and being disengaged from said coupling pin when said chuck portion and said control sleeve are in the release position.

2. The instrument according to claim 1, wherein said control sleeve is spring-biased.

3. The instrument according to claim 1, wherein said groove and said groove-like depression are aligned with each other in said coupled position and are out of alignment in said release position.

4. The instrument according to claim 2, wherein said slots extend along the axis of elongation of said shaft and each has at one end an opening coinciding with an end of said control sleeve and an opposite closed end.

5. The instrument according to claim 4, wherein the slots each have upper portions which include open ends and are offset from aligned axes of said sleeve and said shaft, and lower portions which include the closed ends and are less offset from the aligned axes, said slots also having middle portions intermediate the upper and lower portions which are less offset from the aligned axes than the upper portions and are more offset from the aligned axes than the lower portions, said coupling pin in said coupled position engaging at each end thereof the middle portion of the corresponding slot, the spring biased control sleeve forcing the coupling pin into engagement with the aligned depressions of said shank and said chuck portion.

6. The instrument according to claim 5, wherein the coupling pin in said release position is disposed in the upper portions of the slots and is spaced away from the depressions.

7. The instrument according to claim 6, wherein said rod has openings spaced from said chuck portion and aligned with regions in both said slots adjacent their closed ends, and wherein a second pin is disposed in said openings and in said regions to prevent rotation of the rod in the control sleeve.

8. The instrument according to claim 7, wherein said actuating ring is disposed concentrically about said shaft, said actuating ring, when the push-buttons are depressed being slidable along said shaft away from a tool receiving end thereof to a position at which said chuck portion and said sleeve are in the release position and the actuating ring, when the push-buttons are released, being slidable along the shaft toward the tool receiving end to another position at which said chuck portion and said sleeve are in the coupled position.

9. A dental instrument comprising:
   a tool having an upper portion for use in contacting teeth and a lower portion defining a shank;
   a hollow elongated gripping shaft having an opening at one end;
   tool receiving chuck means provided in said shaft to removably receive said shank;

coupling means including a coupling pin positioned in said chuck means, a control sleeve displaceably mounted on said chuck means and cooperating with said coupling pin, and an actuating sleeve cooperating with said control sleeve to move said coupling pin for coupling said chuck means with said tool and said control sleeve in a lock position in such a manner that the tool is locked immovably in said chuck means in position for use and releasing said chuck means from said control sleeve in a release position at which the tool can be removed from the chuck means; and manually operated push-button means provided on said gripping shaft and operated to act on said actuating sleeve to displace said control sleeve so as to enable said chuck means which is normally in said lock position to be placed in said release position.

10. The instrument according to claim 9, wherein the shank and the chuck means have coincident longitudinal axes when the shank is disposed in the chuck means, said coupling pin being disposed in the chuck means at right angles to said axes, said shank including a first groove-like depression adjacent a lower end thereof and being parallel to said coupling pin, the first depression being engaged by the coupling pin in said lock position and being disengaged from the coupled pin in said release position.

11. The instrument according to claim 10, wherein the chuck means includes a rod with a shank-receiving portion at one end, the shank-receiving portion having a second groove-like depression, the first and second depressions being aligned with each other in said lock position and being out of alignment in said release position.

12. The instrument according to claim 11, wherein the control sleeve is spring-biased and slidable in the direction of elongation of said rod in two opposite directions.

13. The instrument according to claim 12, wherein the control sleeve has two oppositely disposed elongated slots extending in an axial direction of the rod, each of said slots having at one end an opening coincident with an end of the control sleeve and an opposite closed end.

14. The instrument according to claim 13, wherein the slots each have upper portions which include open ends and are offset from aligned axes of said sleeve and said shaft, and lower portions which include the closed ends are are less offset from the aligned axes, said slots also having middle portions intermediate the upper and lower portions which are less offset from the aligned axes than the upper portions and are more offset from the aligned axes than the lower portions, the coupling pin in said lock position engaging at each end thereof the middle portion of the corresponding slot, the spring-biased control sleeve forcing the coupling pin into engagement with the depressions of the shank and the shank receiving portion.

15. The instrument according to claim 14, wherein the coupling pin in said release position is disposed in the upper portions of the slots and is spaced away from the depressions.

16. The instrument according to claim 15, wherein said rod has openings spaced from the shank-receiving portion and aligned with regions in both said slots adjacent their closed ends, and wherein a second pin is disposed in said openings and in said regions to prevent rotation of the rod in the control sleeve.

17. The instrument according to claim 16, and further including an actuating ring disposed concentrically of said shaft, the actuating ring, when the push-button means are depressed being slidable along the shaft away from a tool receiving end thereof to a position at which the instrument is in said release position, and the actuating ring, when the push-button means are released, being slidable along the shaft toward the tool receiving end to another position at which the instrument is in said lock position.

* * * * *